US010213464B2

(12) United States Patent
Freissmuth et al.

(10) Patent No.: US 10,213,464 B2
(45) Date of Patent: Feb. 26, 2019

(54) METHOD FOR ENHANCING ENGRAFTMENT OF HAEMATOPOETIC STEM CELLS

(75) Inventors: Michael Freissmuth, Vienna (AT); Eva-Maria Zebedin-Brandl, Vienna (AT); Christian Bergmayr, Vienna (AT); Filza Hussain, Vienna (AT)

(73) Assignee: SCIPHARM SARL, Mertert (LU)

( * ) Notice: Subject to any disclaimer, the term of this patent is extended or adjusted under 35 U.S.C. 154(b) by 1408 days.

(21) Appl. No.: 13/979,332

(22) PCT Filed: Jan. 13, 2012

(86) PCT No.: PCT/EP2012/050484
§ 371 (c)(1),
(2), (4) Date: Sep. 11, 2013

(87) PCT Pub. No.: WO2012/095511
PCT Pub. Date: Jul. 19, 2012

(65) Prior Publication Data
US 2013/0344038 A1 Dec. 26, 2013

(30) Foreign Application Priority Data
Jan. 13, 2011 (EP) ..................... 11150835

(51) Int. Cl.
*A61K 35/28* (2015.01)
*A61K 31/5585* (2006.01)
*C12N 5/0789* (2010.01)

(52) U.S. Cl.
CPC .......... *A61K 35/28* (2013.01); *A61K 31/5585* (2013.01); *C12N 5/0647* (2013.01); *C12N 2501/01* (2013.01); *Y02A 50/471* (2018.01)

(58) Field of Classification Search
CPC ............... A61K 35/28; A61K 2300/00; A61K 2035/124; A61K 31/40; A61K 31/403; A61K 31/497; A61K 31/506; A61K 31/519; A61K 31/522; A61K 31/5585; C12N 2501/01; C12N 5/0647; C12N 2501/02; C12N 2501/734; C12N 5/0669; Y02A 50/471
See application file for complete search history.

(56) References Cited

U.S. PATENT DOCUMENTS 6,242,482 B1 * 6/2001 Shorr ............... A61K 9/0073 514/469
6,765,117 B2 7/2004 Moriarty et al.
2007/0065414 A1 * 3/2007 Freyman ............ A61K 31/28 424/93.7

FOREIGN PATENT DOCUMENTS

| EP | 2305653 A1 | 4/2011 |
| WO | WO 2006/017169 | 2/2006 |
| WO | 2007/112084 A2 | 10/2007 |
| WO | WO 2008070310 A2 * | 6/2008 ........... A61K 31/557 |
| WO | 2010/036798 A1 | 4/2010 |
| WO | 2010/054271 a1 | 5/2010 |
| WO | 2010/108028 A2 | 9/2010 |
| WO | WO 2011/015630 | 2/2011 |

OTHER PUBLICATIONS

Derchi, et al., Efficacy and safety of sildenafil in the treatment of severe pulmonary hypertension in patients with hemoglobinopathies, Haematologica, 2005, vol. 90, pp. 452-458.*
Mubarak (2010) Respiratory Medicine 104: 9-21.*
Kazemi et al. (2016) Mol. Pharmacol. 89 (6): 630-644.*
Smadja et al, "Treprostinil increases the number and angiogenic potential of endothelial progenitor cells in children with pulmonary hypertension", Angiogenesis. Mar. 2011; 14 (1): 17-27.
International Search Report, International Patent Application No. PCT/EP2012/050484, dated Apr. 12, 2012.
International Written Opinion, International Patent Application No. PCT/EP2012/050484, dated Apr. 12, 2012.
International Preliminary Report on Patentability, International Patent Application No. PCT/EP2012/050484, dated Jul. 16, 2013.
European Search Report, European Patent Application No. 11150835. 4, dated Jul. 22, 2011.
Adams GB, et al., Nature, vol. 459, No. 7243, 2009, pp. 103-107.
Aksentijevich I, et al., Cancer Biother Radiopharm, vol. 17, 2002, pp. 399-403.
Aronoff DM, et al., J Immunol, vol. 178, 2007, pp. 1628-1634.
Awedan AA, Ann Transplant, vol. 7, 2002, pp. 38-43.
Crutchley D J, et al, Jurnal of Pharmacology and Experimental Therapeutics, vol. 271, No. 1, 1994, pp. 446-451.
Dexter TM, Blood, vol. 65, 1985, pp. 1544-1548.
Freissmuth M, et al., J Biol Chem, vol. 264, 1989, pp. 21907-21914.
Goessling W, et al., Cell Stem Cell, vol. 8, No. 4, 2011, pp. 445-458.
Goessling W, et al., Cell, vol. 136, 2009, pp. 1136-1147.
Hoggatt J, et al., Blood, vol. 113, No. 22, 2009, pp. 5444-5455.
Ishii M, et al., Atherosclerosis, vol. 206, No. 1, 2009, pp. 109-118.
Johnson RA, et al., Methods in Enzymology, vol. 238, 1994, pp. 31-56.
Kiriyama M, et al., Br J Pharmacol, vol. 122, 1997, pp. 217-224.
Kudlacek O, et al., J Biol Chem, vol. 276, 2001, pp. 3010-3016.
Long MW, et al., Hematol., vol. 16, 1988, pp. 195-200.
Madonna R, European Heart Journal, vol. 27, No. 17, 2006, pp. 2054-2061.

(Continued)

*Primary Examiner* — Lisa J Hobbs
(74) *Attorney, Agent, or Firm* — Loza & Loza, LLP; Michael F. Fedrick

(57) ABSTRACT

The present invention provides a novel method for enhancing engraftment of haematopoetic stem cells by an ex-vivo pretreatment comprising the steps of obtaining a sample containing haematopoetic stem cells and admixing a prostacyclin analog to obtain a mixture, incubating said mixture for a period of time sufficient to stimulate G alphas-signalling in said cells and optionally and isolating said stimulated cells. Further, a composition comprising a prostacyclin analog for use in the treatment of individuals undergoing haematopoetic stem cell transplantation is provided.

14 Claims, 7 Drawing Sheets

(56) References Cited

OTHER PUBLICATIONS

Figure 2:
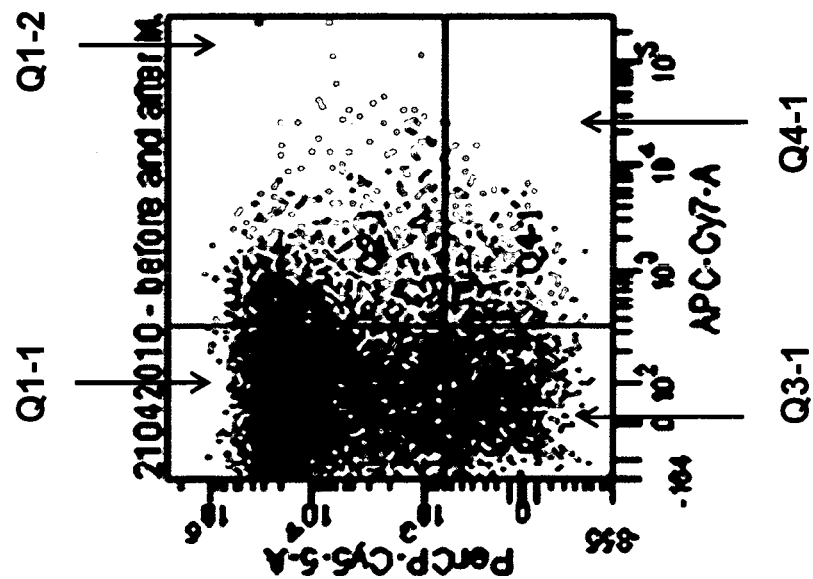

North T E, et al., Nature, vol. 447, No. 7147, 2007, pp. 1007-1011.
Otsuka H, et al., Annals of Vascular Surgery, vol. 20, No. 5, 2006, pp. 646-652.
Ponsiouen B, et al., Embo Reports, vol. 5, No. 12, 2004, pp. 1176-1180.
Sunahara RK, et al., Annu Rev Pharmacol Toxicol, vol. 36, 1996, pp. 461-480.
Tesmer JJ, et al., Science, vol. 278, 1997, pp. 1907-1916.
North et al, "Prostaglandin E2 Is a Potent Regulator of Vertebrate Hematopoietic Stem Cell Homeostasis". Blood Journal, vol. 108 Issue 11 pp. 680-680, 2006.

* cited by examiner

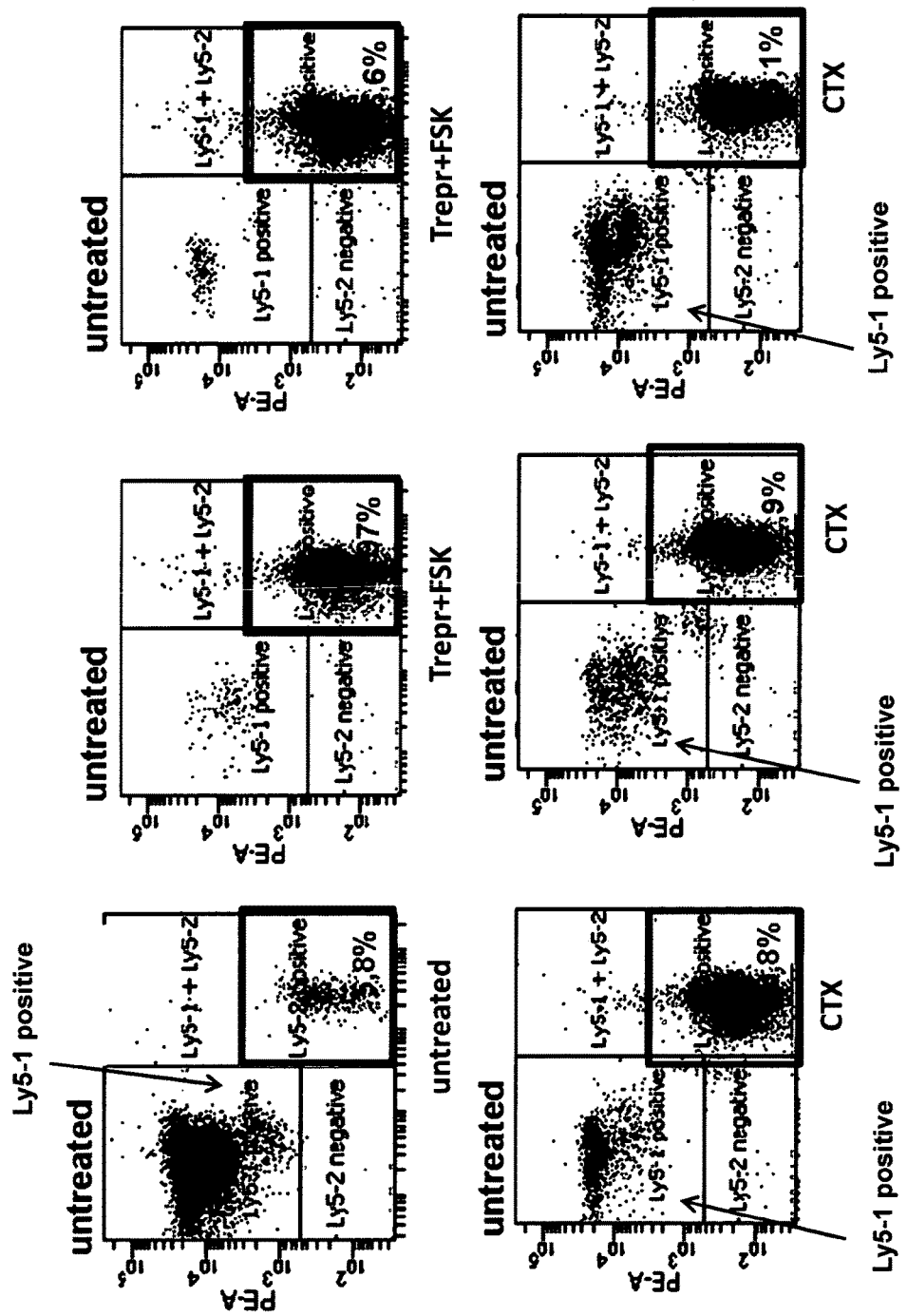

METHOD FOR ENHANCING ENGRAFTMENT OF HAEMATOPOETIC STEM CELLS

CROSS-REFERENCE TO RELATED APPLICATIONS

This application is the U.S. national stage of International Patent Application No. PCT/EP2012/050484, filed on Jan. 13, 2012 and entitled METHOD FOR ENHANCING ENGRAFTMENT OF HAEMATOPOETIC STEM CELLS, which claims the benefit of priority under 35 U.S.C. § 119 from European Patent Application No. 11150835.4, filed Jan. 13, 2011. The disclosures of the foregoing applications are incorporated herein by reference in their entirety.

FIELD OF THE INVENTION

The present invention provides a novel method for enhancing engraftment of haematopoetic stem cells by an ex-vivo pretreatment comprising the steps of obtaining a sample containing haematopoetic stem cells and admixing a prostacyclin analogue to obtain a mixture, incubating said mixture for a period of time sufficient to stimulate G alpha$_s$-signalling in said cells and optionally isolating said stimulated cells.

Further, a composition comprising Treprostinil for use in the treatment of individuals undergoing haematopoetic stem cell transplantation is provided.

Hematopoietic stem cells (HSCs) are primitive cells capable of regenerating all blood products throughout the life of an individual, balancing their self-renewal with progeny differentiation. HSCs transition in location during development and circulate in mammals throughout life, moving into and out of the bloodstream to engage bone marrow niches in sequential steps of homing, engraftment and retention. Homing is the process by which the donor stem cells find their way to the bone marrow, engrafting of stem cells means their growth in bone marrow.

Hematopoietic stem cells have therapeutic potential as a result of their capacity to restore blood and immune cells in transplant recipients. Furthermore, HSCs have the potential to generate cells for other tissues such as brain, muscle and liver. Human autologous and allogeneic bone marrow transplantation methods are currently used as therapies for diseases such as leukemia, lymphoma, and other life-threatening diseases. For these procedures, a large amount of donor bone marrow must be isolated to ensure that there are enough HSCs for engraftment.

Haematopoetic stem cells need a G$\alpha_s$-transduced signal in vivo to populate the bone marrow niche (1). These recent findings confirm earlier in vitro experiments, which showed that the activation of G$\alpha_s$ promote the survival and differentiation of haematopoetic stem cells (2,3). G$\alpha_s$ is the guanine nucleotide binding α-subunit of the heterotrimeric G protein that stimulates all 9 isoforms of membrane-bound mammalian adenylyl cyclase. G$\alpha_s$ can be constitutively activated ex vivo/in vitro by treating the cells with cholera toxin, because cholera toxin APD-ribosylates the catalytic arginine residue (R$^{186/187/201/202}$, the precise number of the arginine depends on the splice variant of G$\alpha_s$); an intact arginine residue is required for GTP-hydrolysis and the resulting deactivation of G$\alpha_s$ (4). Enhanced engraftment can indeed be observed after pretreatment of haematopoetic stem cells with cholera toxin: there were about twice as many (Lin$^-$) precursor cells in the bone marrow, if the stem cell preparation had been pretreated with cholera toxin (1).

However, for stem cell preparation for patients undergoing bone marrow transplantation, cholera toxin would be highly disadvantageous. Cholera toxin (CT), esp. its non-toxic B subunit pentamer moiety (CTB) is a mucosal adjuvant having strong immunomodulatory properties both in vivo and in vitro and is one of the most potent mucosal immunogens. Cholera toxin and CTB stimulate a strong intestinal IgA antibody response and long-lasting immunological memory. Based on this, CTB has become an important component in recently developed oral vaccines against cholera and diarrhea caused by enterotoxigenic E. coli. The strong immunogenicity of CT and CTB can to a large extent be explained by their ability to bind to receptors on the intestinal mucosal surface.

Additionally, during the natural course of the infection the pentameric part B of the toxin molecule binds to the surface of intestinal epithelium cells and is rapidly endocytosed together with the A subunit. Once endocytosed, the catalytically active A-subunit detaches from the pentameric part B and enters the cell via a pore that is formed by the B-subunit. Once inside the cell, it permanently ribosylates the Gs alpha subunit of the heterotrimeric G protein resulting in constitutive cAMP production. This in turn leads to secretion of H$_2$O, Na$^+$, K$^+$, Cl$^-$, and HCO$_3^-$ into the lumen of the small intestine resulting in rapid dehydration and other factors associated with cholera. If injected intravenously, cholera toxin is taken up by most cells (only cells such as the blood brain barrier are shielded by specific barriers). Accordingly, it will raise cAMP in most body cells and cause a large range of side effects (ranging from tachycardia to vasodilation, muscle tremor, hyperglycaemia etc.).

Thus, these effects make cholera toxin unfeasible for human use with regard to stimulation of haematopoetic stem cells.

The therapeutic relevance of stimulating stem cells is however important when undergoing heterologous bone marrow transplantation (i.e., haematopoetic stem cells harvested from immunocompatible donors) and is a standard procedure that is used for the treatment of people suffering from leukaemia, for the treatment of people with genetic defects in the blood cell compartment (e.g., haemoglobinopathies such as thalassaemia; defects in neutrophil granulocyte function etc.).

It is also important as autologous bone marrow transplantation is a standard procedure that is used to increase the therapeutic window of cytotoxic drugs and thus to allow for high dose intensity chemotherapy (5,6).

Haematopoetic stem cells express all four prostaglandin E receptors (EP1-4). The pretreatment of haematopoetic stem cells with (dimethylated) prostaglandin E2 enhances their engraftment (7,8). This effect is mediated by canonical G$\alpha_s$-dependent signalling, because the cAMP-induced activation of protein kinase A (PKA) synergizes with Wnt-dependent signals to stabilize β-catenin (9).

Implantation of autologous bone marrow (BM) mononuclear cells (MNCs) could be enhanced by Beraprost sodium in a rabbit model according to Otsuka et al. The aim of the study was to support artery development in peripheral and myocardial ischemia. Haemopoietic stem cells, however, are a specific type of cells within the bone marrow cells (16).

A combination of stem cell therapy and pharmacological treatments is described by Madonna et al., wherein prostacyclin is tested in ADSC myocardial engrafting after intracoronary administration (17).

Ishii M. et al. disclose that sustained release of prostacyclin enhanced the proangiogenic function of mesenchymal stem cells and muscle cell growth in ischemic tissue (18).

WO2006/017169 describes an implatable sensor with a biocompatible coating for controlling tissue growth which may contain, amongst others, prostacyclin-analogs.

The inhibitory effect of Cicaprost or Iloprost on the synthesis of tissue factor, tumor necrosis factor and interleukin-1ß in human THP1 cells is described in Crutchley D. et al. (19).

The localization of stem cells following transplantation is a critical determinant of success of the transplantation. At present, a high number of stem cells is needed for transplantation because stem cells are not successfully engrafted in the bone marrow and there is a long period of bone marrow aplasia leading to a decrease of mature blood cells.

It is thus still an unmet need to provide methods and compositions to stimulate HSCs to increase homing, engraftment and retention of isolated HSCs to bone marrow niches of subjects undergoing bone marrow transplantations.

The problem is solved by the embodiments of the present invention.

BRIEF DESCRIPTION OF THE INVENTION

It has been surprisingly shown that the synthetic prostacyclin 12 ($PGI_2$) analogues like for example Treprostinil, Iloprost, Beraprost and Cicaprost are capable of increasing cAMP levels in haematopoetic stem cells which leads to increased engraftment of stem cells in bone marrow.

A prostacyclin analogue like Treprostinil offers several advantages over prostaglandin E2:

(i) It is a stable analogue of prostacyclin/$PGI_2$, which also stimulates EP2- and EP4-receptors (10). Thus it has the potential to stimulate multiple $G_s$-coupled receptors while not engaging inhibitory (i.e., $G_i$-coupled) $EP_3$-receptors, which inhibit cAMP accumulation. For the latter, dimethyl-$PGE_2$ is a full agonist (1). In contrast, Treprostinil is only a low affinity agonist at EP3-receptors.

(ii) Because they are metabolically more stable than natural prostacyclins, Treprostinil, Iloprost, Beraprost and Cicaprost can elicit more long lasting effects if applied in vivo and thus support more efficient bone marrow engraftment.

(iii) Prolonged/repeated administration of a prostacyclin analogue, specifically of Treprostinil, Iloprost, Beraprost and Cicaprost are well tolerated.

The present invention provides a novel method for enhancing engraftment of haematopoetic stem cells by an ex-vivo pretreatment which comprises the steps of
  a. obtaining a sample containing haematopoetic stem cells and
  b. admixing at least one prostacyclin analogue to obtain a mixture
  c. incubating said mixture for a period of time sufficient to stimulate G alpha$_s$-signalling in said cells and optionally
  d. isolating and optionally purifying said stimulated cells.

According to an embodiment of the invention, the prostacyclin analogue is selected from the group of Treprostinil, Iloprost, Cicaprost and Beraprost or pharmaceutically acceptable salts thereof.

According to the inventive method, a mixture of stimulated and unstimulated stem cells can also be provided.

Specifically, the sample is bone marrow. The stem cells can generally be of any source known, specifically they can be HSCs isolated from peripheral blood, cord blood or bone marrow.

According to the invention, Treprostinil can be a derivative selected from the group of acid derivatives, prodrugs, polymorphs or isomers.

Similarly, Iloprost, Cicaprost or Beraprost can be derivatives from the group of acid derivatives, prodrugs, polymorphs or isomers therefrom.

According to an alternative embodiment of the invention, the sample may be admixed with at least one prostacyclin analogue together with an unspecific cAMP activating agent, preferably selected from cholera toxin and forskolin.

According to a specific embodiment of the invention, a composition comprising a prostacyclin analogue is provided for use in the treatment of individuals suffering from bone marrow diseases which may undergo haematopoetic stem cell transplantation.

According to a specific embodiment of the invention, the prostacyclin analogue of the composition is selected from the group of Treprostinil, Iloprost, Cicaprost or Beraprost or pharmaceutically acceptable salts thereof.

According to a preferred embodiment, the composition comprises Treprostinil.

Specifically, the individuals are suffering from leukaemia, a defect of the blood cell compartment, bone marrow transplantation after chemotherapy or irradiation.

According to a further embodiment of the invention, the defect of the blood cell compartment is haemoglobinopathy or a defect in neutrophil granulocyte function.

The composition of the invention can also be used for the treatment of individuals suffering from a bone marrow disease which are undergoing haematopoetic stem cell transplantation by administering a prostacyclin analogue for at least seven days after bone marrow transplantation. Specifically, a prostacyclin analogue selected from the group of Treprostinil, Iloprost, Cicaprost and Beraprost is used, more specifically, Treprostinil.

According to a further embodiment, a composition comprising a prostacyclin analogue and stimulated haematopoetic stem cells is provided.

According to a further embodiment, a composition comprising Treprostinil or a pharmaceutically acceptable salt thereof and stimulated haematopoetic stem cells is provided.

Specifically for use in animals or animal studies, the compositions of the invention can further comprise forskolin or cholera toxin.

The inventive compositions can be pharmaceutical compositions.

The inventive composition can be administered by all routes known in the art, specifically it is prepared for intravenous or subcutaneous administration.

The prostacyclin analogue can be provided in an orally available form selected from the group of sustained release forms, tablets or capsules.

The amount of the prostacyclin analogues depends on the therapeutic application or method for preparing stimulated HSCs. Very specifically, for therapeutic applications, the effective amount of Treprostinil is at least 1.0 ng/kg of body weight.

FIGURES

Figure 1:
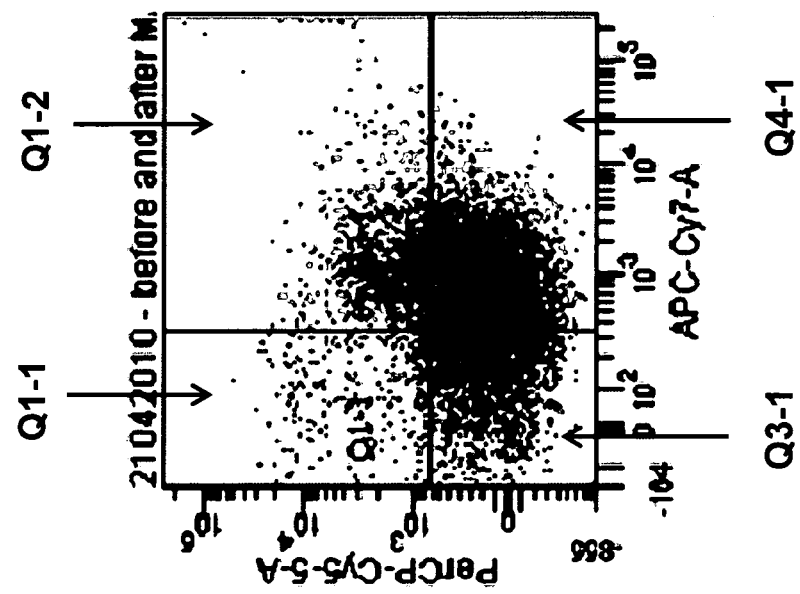

FIG. 1: Characterization of the $Lin^+$ cell population retained by the magnetic beads. The x-axis (labelled APC-C7-A) denotes the fluorescence recorded by the mixture of antibodies directed against lineage markers: CD3ε for T-cells, CD45R(=B220) for B-cells, CD11b and Ly-6G/Ly-6C (Gr-1) for the myeloid (monocytic/granulocytic) lineage, Ter-119 for the erythroid lineage. The y-axis is the fluorescence recorded for the antibody against the murine stem cell factor receptor c-Kit. It is evident that the upper left quadrant (denoting c-Kit+ and lineage marker-negative cells) is depleted of cells.

FIG. 2: Characterization of the Lin⁻ cell population that did not bind to the magnetic beads. As in FIG. 1, the x-axis (labelled APC-C7-A) denotes the fluorescence recorded by the mixture of antibodies directed against lineage markers: CD3ε for T-cells, CD45R(=B220) for B-cells, CD11b and Ly-6G/Ly-6C (Gr-1) for the myeloid (monocytic/granulocytic) lineage, Ter-119 for the erythroid lineage. The y-axis is the fluorescence recorded for the antibody against the murine stem cell factor receptor c-Kit. It is evident that the lower quadrant (denoting c-Kit-negative and lineage marker-positive cells) is depleted of cells and that cells are predominantly found in the left upper quadrant where the c-Kit-positive and lineage marker-negative cells are to be expected.

Figure 3:
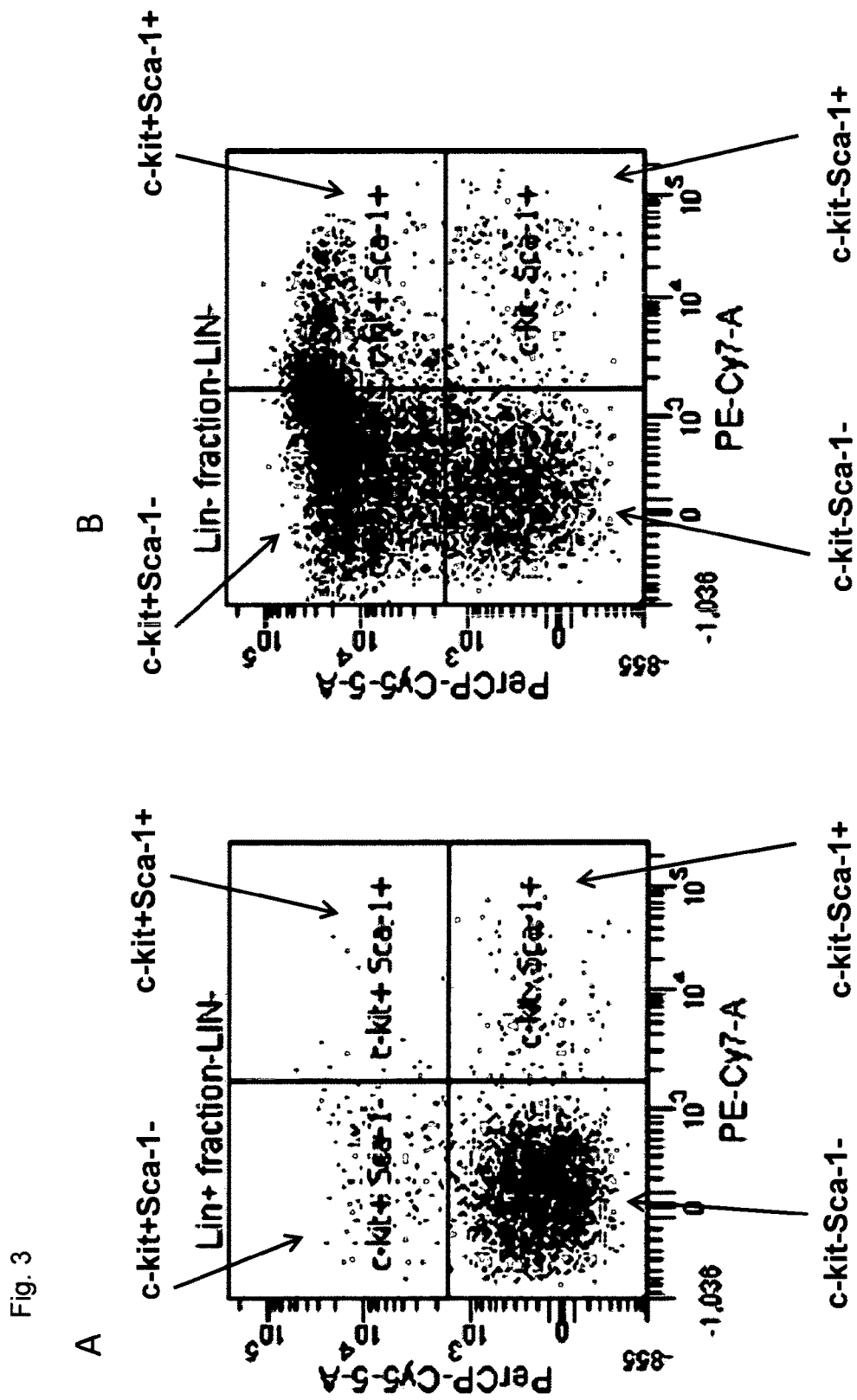

FIG. 3 shows the characterization of the Lin⁺ (FIG. 3A) and Lin⁻ cell populations (FIG. 3B) for the presence of Sca-1 and c-Kit. Panels 3A and 3B show the cells retained on magnetic beads (characterized in FIG. 1) and that appeared in the flow through (characterized in FIG. 2). These were stained as outlined in the methods section and analyzed simultaneously for the presence of c-Kit (PerCP-Cy5-5-A, y-axis) and of Sca-1 (PE-Cy7-A, x-axis). It is evident that the lineage positive cells analyzed in panel A are found in the left lower quadrant, i.e. they are devoid of both, c-Kit and sSca-1. In contrast, cells in Panel B are predominantly in the upper quadrants, i.e. they have high levels of either c-Kit (left upper quadrant) or of both, c-Kit and Sca-1 (upper right quadrant) as expected for the haematopoetic stem cell population and of non-committed progenitors.

Figure 4:
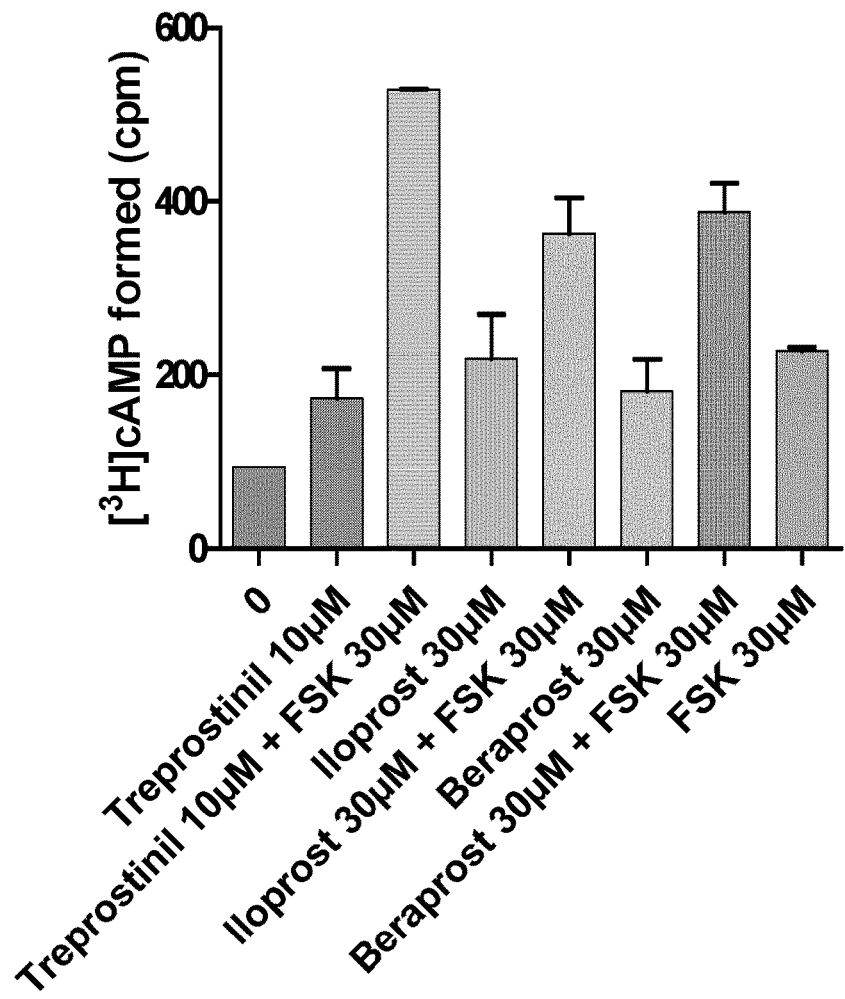

FIG. 4: Cyclic AMP accumulation in (Lin⁻, c-Kit⁺, Sca-1⁺) haematopoetic stem cells after stimulation by forskolin, Treprostinil, Iloprost Berapost or the combination of forskolin and prostanoids. Lin⁻ cells (7*10⁵/assay) were incubated in the presence of [³H]adenine to metabolically prelabel the adenine nucleotide pool as outlined under *Methods*. The cells were incubated in the absence (left hand column labelled 0) and presence of the indicated compounds. The accumulated [³H]cAMP was purified by sequential chromatography on Dowex AG50-X8 and alumina columns and quantified by liquid scintillation counting. Data are means±S.D. (n=4).

Figure 5:
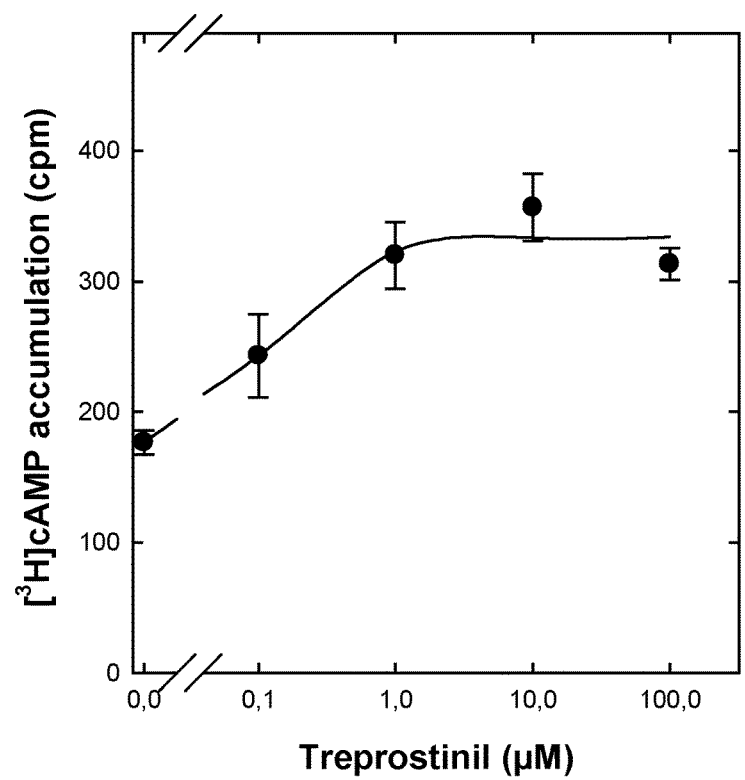

FIG. 5: Concentration-response curve for Treprostinil-induced cAMP accumulation in (Lin⁻, c-Kit⁺, Sca-1⁺) haematopoetic stem cells. Assay conditions were as outlined in the legend to in FIG. 4. Data are means±S.D. (n=2).

Figure 6:
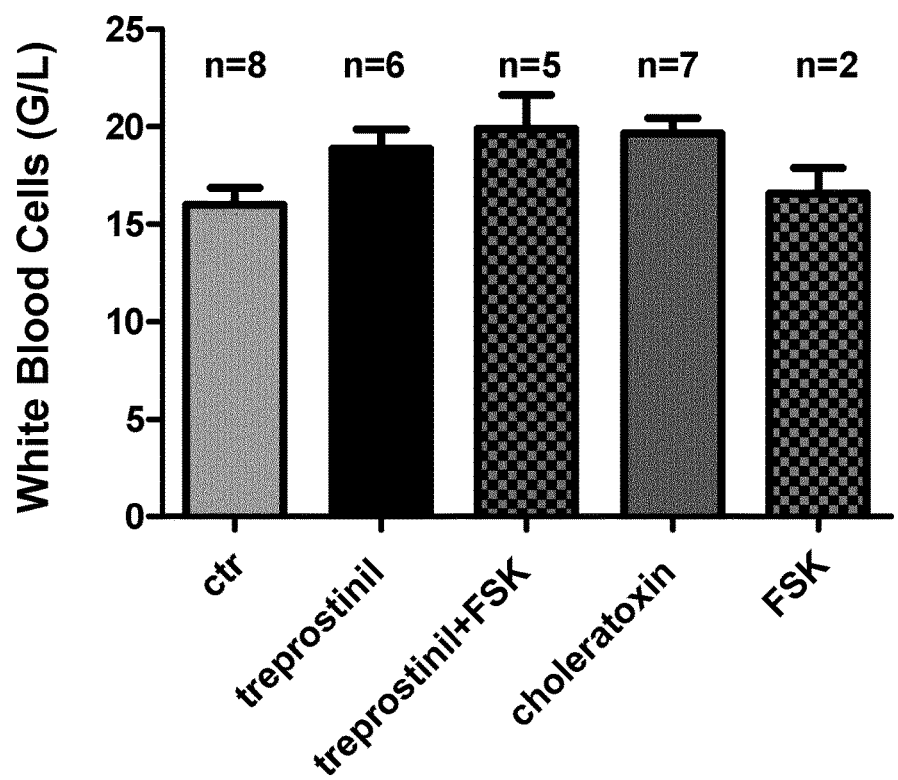

FIG. 6. Ex vivo treatment of haematopoetic stem cells with Treprostinil results in enhanced engraftment of bone marrow in lethally irradiated mice. Haematopoetic stem cells prepared as in FIG. 3 were pretreated with the indicated compounds (FSK, forskolin) as outlined under *Methods*. White blood cell count was determined by FACS. The number of animals investigated is indicated.

Figure 7:
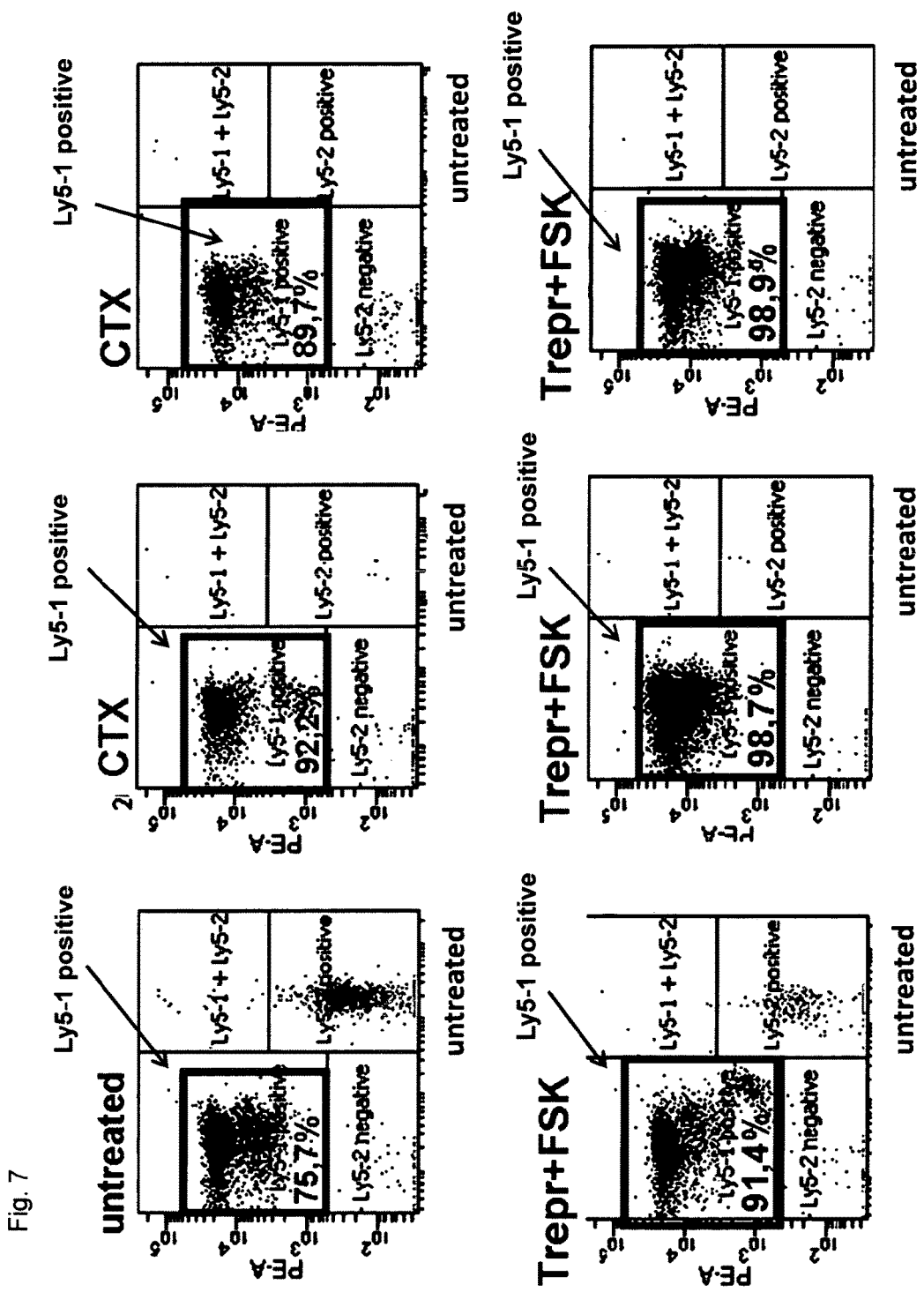

FIG. 7: Ratio of Ly5.2 and Ly5.1 positive blood cells 16 weeks after bone marrow transplantation. Ly5.1 cells were pretreated with CTX or Treprostinil and Forskolin.

FIG. 8: Ratio of Ly5.2 and Ly5.1 positive blood cells 16 weeks after bone marrow transplantation. Ly5.2 cells were pretreated with CTX or Treprostinil and Forskolin.

DETAILED DESCRIPTION OF THE INVENTION

Providing methods and means to increase homing and engrafting of HSCs to the bone marrow environment has strong biologic and medical implications. The localization of stem cells following transplantation is highly important for clinical procedures as currently massive numbers of stem cells are required in clinical transplantation thus leading to the need of high amounts of donor cells. Such methods are also highly useful because a significant number of autologous donor transplants contain insufficient numbers of stem cells, or HSCs. Likewise, patients are often unable to find histocompatible donors, emphasizing the need for methods and compositions for reducing the number of HSCs needed for successful transplantation. The ability to improve homing and engrafting of HSCs in vitro or ex vivo allows the collection of fewer cells from donors, thereby reducing the time and discomfort associated with bone marrow/peripheral stem cell harvesting, and increasing the pool of willing HSC donors.

The present invention thus provides a novel method for enhancing engraftment of HSCs by an ex-vivo pretreatment of the HSCs comprising the steps of a) obtaining a sample containing haematopoetic stem cells and b) admixing at least one prostacyclin analogue to obtain a mixture, c) incubating said mixture for a period of time sufficient to stimulate G alpha$_s$-signalling in said cells and d) optionally isolating said stimulated cells or using said mixture containing said stimulated cells for further use, for example for treatment or transplantation.

Specifically, the prostacyclin analogue is selected from the group of Treprostinil Iloprost, Beraprost and Cicaprost or pharmaceutically acceptable salts thereof.

Treprostinil is a synthetic analogue of prostacyclin. Treprostinil is marketed as Remodulin™. Treprostinil is a (1R,2R,3aS,9aS)-[[2,3,3a,4,9,9a-hexahydro-2-hydroxy-1-[(3S)-3-hydroxyoctyl]-1H-benz[f]inden-5-yl] oxy]acetic acid monosodium salt.

Iloprost is marketed as "Ilomedine" and is a 5-{(E)-(1S, 5S,6R,7R)-7-hydroxy-6[(E)-(3S, 4RS)-3-hydroxy-4-methyl-1-octen-6-inyl]-bi- cyclo[3.3.0]octan-3-ylidene}pentanoic acid.

Beraprost is a 2,3,3a,8b-tetrahydro-2-hydroxy-1-(3-hydroxy-4-methyl-1-octen-6-ynyl)-1H-cyclopenta(b)benzofuran-5-butanoic acid.

Cicaprost is a 2-[(2E)-2-[(3aS,4S,5R,6aS)-5-hydroxy-4-[(3S,4S)-3-hydroxy-4-methylnona-1,6-diynyl]-3,3a,4,5,6, 6a-hexahydro- 1H-pentalen-2-ylidene]ethoxy]acetic acid.

According to an inventive embodiment, at least two, specifically at least three different prostacyclin analogues can be used for said method. Alternatively, two, three, four, five or six or even more different prostacyclin analogues can be used for said method.

This method advantageously provides stimulated stem cells which can directly be administered to individuals and which do not show any unwanted side effects due to high amounts of unselective cAMP activating agents.

According to a further embodiment of the invention a method for enhancing engraftment of haematopoetic stem cells by an ex-vivo pretreatment is provided which comprises following steps:

a. obtaining a sample containing haematopoetic stem cells and b. admixing a prostacyclin analogue and forskolin to obtain a mixture c. incubating said mixture for a period of time sufficient to stimulate G alpha$_s$-signalling in said cells and optionally d. isolating said stimulated cells and optionally e. purifying and/or concentrating said stimulated cells.

According to a specific embodiment of the invention, the ratio of prostacyclin analogue and forskolin may be about 1:3. The HSCs treated with forskolin and prostacyclin analogues may be purified before being reimplanted, however, these HSCs may also be re-implanted without further purification steps as low amounts of forskolin may be present but may not cause any negative side effects.

Alternatively, a combination of Treprostinil with one of Iloprost, Beraprost or Cicaprost can be added to the stem cells. Alternatively, Treprostinil can be admixed in combination with more than one, for example with two, three, four or five of other prostacyclin analogues, for example, but not limited to Iloprost, Beraprost or Cicaprost or physiologically acceptable salts thereof.

According to a specific embodiment for use in animal studies or treatment of animals, a cAMP enhancer like forskolin and/or cholera toxin can be additionally admixed to the HSCs or HSC/Treprostinil, Iloprost, Cicaprost or Beraprost mixture before incubation.

The period of time which is needed to stimulate the G alpha$_s$-signalling in said cells can be measured according to known methods, for example by using cAMP measurements of which there are many variations: RIA, Fluorescence Resonance Energy Transfer (FRET) with EPAC (epac1) (Ponsiouen B. et al., EMBO reports, 5, 12, 1176-1180 (2004)), radiochemical methods etc. Stimulated cells wherein G alpha$_s$-signalling is occurring can be selected or discriminated or isolated from unstimulated cells by methods known in the art like a FRET-based cAMP reporter.

According to an embodiment of the invention the incubation time is about 1 to 60 min, preferably about 2 to 30 min.

The cAMP-dependent pathway is an essential pathway for promoting engraftment of haematopoetic stem cells. It has been shown by the inventors that a prostacyclin analogue can trigger cAMP elevation in haematopoetic stem cells. It does so by activating multiple receptors, i.e. IP- and EP- receptors thus leading to increased G alpha$_s$-signalling. Accordingly, prostacyclin analogues like Treprostinil, Iloprost, Cicaprost or Beraprost are more effectively raising cAMP levels.

According to a very specific embodiment, Trepostinil is a preferred prostacyclin analogue used according to the method of the present invention.

Alternatively, in certain methods and compositions of the invention, at least one agent selected from a cyclic AMP (cAMP) enhancer or a ligand to a prostaglandin EP receptor may also be added. Examples of cAMP enhancers include, but are not limited to, dibutyryl cAMP (DBcAMP), phorbol ester, forskolin, sclareline, 8-bromo-cAMP, cholera toxin (CT), aminophylline, 2,4 dinitrophenol (DNP), norepinephrine, epinephrine, isoproterenol, isobutylmethyl-xanthine (IBMX), caffeine, theophylline (dimethylxanthine), dopamine, rolipram, prostaglandin E$_1$, prostaglandin E$_2$, pituitary adenylate cyclase activating polypeptide (PACAP), and vasoactive intestinal polypeptide (VIP), among others known in the art can be added to the stem cells or the stem cells/Treprostinil or stem cells/Treprostinil, Iloprost, Cicaprost and/or Beraprost mixture before incubation. Examples of cAMP enhancers also include cAMP and analogs of cAMP, such sp-5,6-DCI-BIMPS (BIMPS), among others.

According to a specific embodiment of the invention, forskolin and/or cholera toxin or the A subunit of cholera toxin are additionally admixed to the stem cells or the stem cells/Treprostinil mixture before incubation.

In a specific embodiment, said cAMP enhancers are used for performing stem cell treatment of animal cells or for performing animal studies in view of stem cell engraftment.

In reference to prostacyclin analogues, according to the present invention the term "prostacyclin analogues" includes also derivatives and analogues of said substances.

The terms "analogue" or "derivative" relate to a chemical molecule that is similar to another chemical substance in structure and function, often differing structurally by a single element or group, which may differ by modification of more than one group (e.g., 2, 3, or 4 groups) if it retains the same function as the parental chemical. Such modifications are routine to skilled persons, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives can also include conjugates, such as biotin or avidin moieties, enzymes such as horseradish peroxidase and the like, and radio-labeled, bioluminescent, chemoluminescent, or fluorescent moieties. Further, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.).

The term "derivative" also includes within its scope alterations that have been made to a parent sequence including additions, deletions, and/or substitutions that provide for functionally equivalent or functionally improved molecules.

According to a specific embodiment of the invention, the Treprostinil derivative is selected from the group of acid derivatives of Treprostinil, prodrugs of Treprostinil, polymorphs of Treprostinil or isomers of Treprostinil.

Similarly, Iloprost, Cicaprost or Beraprost can be derivatives from the group of acid derivatives, prodrugs, polymorphs or isolmers therefrom.

The term "haematopoetic stem cells" (HSCs) or the more general term "stem cells" are understood as equivalent terms in the description of the present invention, and generally relate to either pluripotent or multipotent "stem cells" that give rise to the blood cell types, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art. "Stem cells" are usually characterized by their ability to form multiple cell types (i.e. being multipotent) and their ability for self-renewal. However, oligopotent and unipotent progenitors may be included also. "Haematopoiesis" refers generally to the process of cellular differentiation or formation of specialized blood cells from an HSC. During development, hematopoiesis translocates from the fetal liver to the bone marrow, which then remains the site of haematopoiesis throughout adulthood. Once established in the bone marrow, HSCs are not distributed randomly throughout the bone cavity. Rather, HSCs are typically found in close proximity to the endosteal surfaces. The more mature stem cells increase in number as the distance from the bone surface increases.

Haematopoetic tissues contain cells with long-term and short-term regeneration capacities, as well as committed multipotent, oligopotent, and unipotent progenitors.

The sample containing HSCs specifically can be bone marrow.

HSCs can be obtained by known techniques from any source known to contain HSCs, specifically from peripheral blood, umbilical cord or cord blood, placenta and bone marrow. Alternatively, also sources like fetal liver, fetal spleen, and aorta-gonad-mesonephros) of animals are possible. HSCs from human origin being are preferred for the methods and compositions of the invention.

For example, HSCs may be found in the bone marrow of adults, including femurs, hip, ribs, sternum, and other bones. HSCs may be obtained directly by removal from the hip using a needle and syringe, or from the blood, often following pre-treatment with cytokines, such as G-CSF (granulocyte colony-stimulating factors), that induce cells to be released from the bone marrow compartment.

HSCs may be identified according to certain phenotypic or genotypic markers. For example, HSCs may be identified by their small size, lack of lineage (lin) markers, low staining (side population) with vital dyes such as rhodamine 123 ($rho^{lo}$) or Hoechst 33342, and presence of various antigenic markers on their surface, many of which belong to the cluster of differentiation series (e.g., CD5, CD11 b, CD34, CD38, CD90, CD133, CD105, CD45, GR-1 (=Ly-6G/C), 7-4, Ter-119 and c-kit). HSCs are mainly negative for the markers that are typically used to detect lineage commitment, and, thus, are often referred to as lin(−) cells. Most human HSCs may be characterized as $CD5^+$, $CD45R$ $(6220)^+$, $CD11^+$, $GR-1^+$, $CD34^+$, $CD59^+$, Thyl/$CD90^+$, $CD38^{lo/-}$, C-kit/$CD117^+$, and lin($^−$). However, not all stem cells are covered by these combinations, as certain HSCs are $CD347^+$ and $CD38^+$. Also some studies suggest that earliest stem cells may lack c-kit on the cell surface.

For purification of lin(−) HSCs by flow cytometry, or FACS, an array of mature blood-lineage marker antibodies may be used to deplete the lin(+) cells or late multipotent progenitors (MPP), including, for example, antibodies to CD3epsilon, CD5, CD45R, CD11 b, CD16, GR-1, 7-4 and Ter-119, CD 13, CD32 and CD33, CD71, CD 19, CD61, Mac-1 (CDI lb/CD18), Gr-I, 117Ra, CD3, CD4, CD5, and CD8 among others known in the art. Additional purification methods are known in the art, for example, methods that use the particular signature of the 'signaling lymphocyte activation molecules' (SLAM) family of cell surface molecules.

HSCs, whether from cord blood, bone marrow, peripheral blood, or other source, may be grown or expanded in any suitable, commercially available or custom defined medium, with or without serum. HSCs from human source are preferred embodiments of the invention. For instance, in certain embodiments, serum free medium may utilize albumin and/or transferrin. Further, cytokines may be included, such as Flt-3 ligand, stem cell factor (SCF), and thrombopoietin (TPO), among others. HSCs may also be grown in vessels such as bioreactors. A suitable medium for ex vivo expansion of HSCs may also comprise HSC supporting cells, such as stromal cells (e.g., lymphoreticular stromal cells), which can be derived, for instance, from the disaggregation of lymphoid tissue, and which have been show to support the in vitro, ex vivo, and in vivo maintenance, growth, and differentiation of HSCs, as well as their progeny.

"Cord blood" or "umbilical cord blood" relates generally to a relatively small amount of blood (up to about 180 ml) from a newborn baby that returns to the neonatal circulation. Cord blood is rich in HSCs and may be harvested and stored for later use according to techniques known in the art The terms "ex vivo" or "in vitro" refer to activities that take place outside an organism, such as experimentation or measurements done in or on living tissue in an artificial environment outside the organism, preferably with minimum alteration of the natural conditions. In certain embodiments, such tissues or cells can be collected and frozen, and later thawed for ex vivo treatment. Tissue culture experiments or procedures lasting longer than a few days using living cells or tissue are typically considered to be "in vitro" though this term can be used interchangeably with ex vivo. The recitations "ex vivo administration," "ex vivo treatment," or "ex vivo therapeutic use," relate generally to medical procedures in which one or more organs, cells, or tissues are obtained from a living or recently deceased subject, optionally purified/enriched, exposed to a treatment or procedure to treat the stem cells (e.g., an ex vivo administration step that involves incubating the cells with a composition of the present invention to enhance engrafting capabilities of HSCs), and then administered to the same or different living subject after that optional treatment or procedure.

Such ex vivo therapeutic applications may also include an optional in vivo treatment or procedural step, such as by administering a composition of the invention one or more times to the living subject after administration of the organ, cells, or tissue. Both local and systemic administration is contemplated for these embodiments, according to well-known techniques in the art. The amount of Treprostinil or the amount of mixture containing Treprostinil and stimulated stem cells optionally together with further agents administered to a subject depend on the characteristics of that subject, such as general health, age, sex, body weight, and tolerance to drugs, as well as the degree, severity, and type of reaction to Treprostinil and/or cell transplant.

According to a specific embodiment of the invention, a composition comprising a prostacyclin analogue is provided for use in the treatment of individuals undergoing haematopoetic stem cell transplantation.

According to a preferred embodiment, the composition comprises prostacyclin analogue selected from the group of Treprostinil, Iloprost, Cicaprost and Beraprost or pharmaceutically acceptable salts thereof, more specifically it comprises Treprostinil.

The inventive composition can also comprise Treprostinil together with one or more of Iloprost, Cicaprost or Beraprost. Alternatively the composition can comprise Iloprost in combination with one or more of Treprostinil, Cicaprost or Beraprost or pharmaceutically acceptable salts thereof. Alternatively the composition can comprise Beraprost in combination with one or more of Treprostinil, Cicaprost or Iloprost or pharmaceutically acceptable salts thereof. Alternatively the composition can comprise Cicaprost in combination with one or more of Treprostinil, Beraprost or Iloprost or pharmaceutically acceptable salts thereof.

Said subjects can suffer from any bone marrow disease, i.e. a disease wherein the normal bone marrow architecture is displaced by malignancies, aplastic anaemia, or infections leading to a decrease in the production of blood cells and blood platelets. Said bone marrow disease can be for example leukaemia, a defect of the blood cell compartment or a need for bone marrow transplantation after chemotherapy or irradiation treatment.

More specifically, the defect of the blood cell compartment can be haemoglobinopathy like thalassaemia or defects in neutrophil granulocyte function or a defect in neutrophil granulocyte function.

The use for the treatment of individuals suffering from bone marrow diseases, for example due to chemotherapy or irradiation and thus undergoing haematopoetic stem cell transplantation by administering at least one prostacyclin analogue for a limited period of time after bone marrow transplantation is also covered by the present invention.

The treatment of subjects undergoing bone marrow transplantation using at least one prostacyclin analogue, at least one prostacyclin analogue together with one or more, specifically two, more specifically three cAMP enhancers or a mixture comprising at least one, specifically two, more specifically three prostacyclin analogues and stimulated stem cells optionally together with further agents like one or more cAMP enhancers is covered by the present invention as well.

More specifically, the cAMP enhancer can be forskolin.

At least one prostacyclin analogue can be used for enhancing the engraftment of human HSCs during bone marrow transplantations or upon reconstitution of the bone marrow by using HSCs. Accelerated engraftment shortens the period at which subjects are susceptible to potentially lethal infections, bleeding and other serious complications. Hence, a prostacyclin analogue ought to be a useful therapeutic option to pretreat donor bone marrow to enhance bone marrow engraftment (i.e., by reducing the number of cells required and shortening the duration of bone marrow aplasia).

Specifically, the prostacyclin analogue is selected from the group of Treprostinil, Iloprost, Cicaprost or Beraprost or pharmaceutically acceptable salts thereof. More specifically, Treprostinil is the preferred prostacyclin analogue to be used.

Continuous treatment of subjects for several days after bone marrow transplantation with a prostacyclin analogue ought to result in improved clinical outcome by improving engraftment (i.e., by reducing the number of cells required and shortening the duration of bone marrow aplasia).

Thus, according to a specific embodiment, the treatment is performed at least five days after transplantation, more specifically for at least 10 days, more specifically for at least 14 days after transplantation.

According to an alternative embodiment of the invention, a composition comprising one or more than one prostacyclin analogue and stimulated haematopoetic stem cells is covered.

Alternatively, in certain embodiments, an agent selected from a cyclic AMP (cAMP) enhancer or a ligand to a prostaglandin EP receptor may be added to the composition. According to a specific embodiment, the inventive composition can also comprise forskolin.

Specifically, the compostions of the invention are pharmaceutical compositions. Further pharmaceutically acceptable excipients as known in the art can be contained in said compositions.

The amount of the prostacyclin analogue depends on the therapeutic or method for preparing stimulated HSCs. Very specifically, for therapeutic applications, the effective amount of Treprostinil is at least 1.0 ng/kg of body weight The inventive composition can be administered to the subject by any mode applicable and known in the art. More specifically, intravenous or subcutaneous administration is provided.

Said composition can be in an orally available form selected from the group of sustained release forms, tablets or capsules.

The foregoing description will be more fully understood with reference to the following examples. Such examples are, however, merely representative of methods of practicing one or more embodiments of the present invention and should not be read as limiting the scope of invention.

EXAMPLES

Example 1

Materials and Methods
Isolation of Bone Marrow Stem Cells

Ten mice (C57BL/6) were sacrificed by cervical dislocation. The long bones of the hind limbs (i.e., femora and tibiae) were freed of muscle and connective tissue and flushed with RPMI medium using a syringe and 27½ G needle. The cell suspension was freed from visible connective tissue, collected and transferred to centrifuge tubes. Cells were harvested by centrifugation (1,200 rpm/~100 g for 5 min) and resuspended in 3 mL erythrocyte lysis buffer (0.15 M $NH_4Cl$, 10 mM $KHCO_3$, 0.1 mM EDTA, pH adjusted to 7.2 to 7.4). The cell suspension was incubated for 2 min at 20° C. followed by 4 min on ice. Thereafter, RPMI (10 mL) was added and the cells were harvested by centrifugation and counted. The typical yield of cells was $3*10^7$/mouse.

Cells were resuspended in ice-cold PBS (phosphate buffered saline) containing 2% FCS (fetal calf serum) at a cell density of $2.5*10^8$ cells/mL to which a cocktail of biotinylated antibodies ("Lineage Cell Depletion Kit" of Miltenyi Biotec) containing lineage-specific antibodies directed against CD5, CD45R (B220), CD11b, GR-1 (=Ly-6G/C), 7-4, and Ter-119 at a ratio of 0.1 mL antibody solution per $10^8$ cells. Cells were incubated for 20 min on ice with the antibodies and pelleted by centrifugation. After resuspension ($3.3*10^8$ cells/mL) the second anti-biotin-coated Micro-Beads (0.2 mL/$10^8$ cells, provided with the ("Lineage Cell Depletion Kit" of Miltenyi Biotec) was added to the cell suspension and the mixture was incubated for 15 min on ice. Thereafter, the sample was diluted in MACS-buffer (30 mL), the cells were collected by centrifugation and resuspended in 6 mL of MACS-buffer. This suspension was loaded onto prepacked LS columns, which contain ferromagnetic beads coated with a cell-compatible plastic material. Typically three columns were employed for (2 mL cells suspension/column). The flow-through contained the lineage marker-negative cells ($Lin^-$ cells), while the lineage committed cells were retained on the column. Cells were pelleted by centrifugation and resuspended in mL PBS.

The typical yield was $7*10^5$ $Lin^-$ cells/mouse.

Fluorescence-Activated Cell Sorting (FACS) Analysis

The antibodies employed for staining of cell surface markers were from the following sources: The mouse lineage panel antibodies were from Becton Dickinson Biosciences (BD 559971, containing in biotinylated from anti-CD3ε, anti-CD11b, anti-CD45R, anti-Ly-6G/Ly-6c, anti-Ter-119), the affinity purified rat anti-mouse CD16/CD32 (mouse $Fc\gamma_{II/III}$ block, BD 553142) and the fluorescent dye streptavidin-allophycocyanin-Cy7 (streptavidin APC-Cy7, BD554063) were also from Becton Dickinson Biosciences. Phycoerythrin(PE)-Cy7-labelled anti-mouse Ly6A/E (=stem cell antigen −1=Sca1) PE-Cy7 (catalogue no. 25-5981-82) and PE-Cy5 anti-mouse CD117 (c-Kit) (catalogue no. 15-1171-81) were from eBiosciences.

Directly after MACS, $1*10^6$ lineage positive (Lin+) and negative (Lin−) cells were transferred into FACS tubes and stored on ice in 50 μL PBS. In the meantime, the following FACS antibodies were diluted (1:50) and mixed in PBS: anti CD16/CD32 purified (to block Fc-receptors), biotinylated anti-CD3ε, biotinylated anti-CD11b, biotinylated anti- CD45R, biotinylated anti-Ly-6G/Ly-6C, and biotinylated anti-Ter-119, streptavidin-labelled APC-Cy7, PE-Cy7-labeled anti-Sca-1, PE-Cy5-labeled anti-c-kit. This master mix (50 μL) was added to each sample, which were then mixed by gentle vortexing and incubated at 4° C. in the dark for 15 min. Thereafter, the cells were harvested by centrifugation, washed in 2 mL PBS and resuspended in PBS. Samples were analysed in a FACS Canto II (Becton Dickinson). The gating procedure was as follows: the gates for living cells were set by recording forward and sideward scatter. The living cells were further discriminated based on the expression of lineage markers (i.e., CD11b, CD45R, Ly-6G/Ly-6C, Ter-119). This allowed for defining the gates for Lin$^-$ cells, which were further analyzed for the expression of Sca-1 and c-Kit.

[3H]cAMP Accumulation Assay

Lin$^-$/sca1$^+$-cells were incubated in 1 mL of stem cell medium (Stem Span SFEM, Stem Cell Tech #09650) containing 0.5 mg/L each, benzylpenicillin and streptomycin, 50 ng/mL each murine stem cell factor (mSCF), human Flt-3, hIL-11 50 ng/mL, m-IL3 (10 ng/mL) (all from PreProTech) 10 μg/mL adenosine deaminase (Roche) and [$^3$H]adenine (Perkin Elmer, 1 μCi/mL). The preincubation lasted for 4 h at 37° C. The cells were then stimulated with the compounds (forskolin, treprostinil and other prostanoids; cholera toxin) for 1 h. The cells were then pelleted (5 min at 100 g), the medium was removed and the pellet was lysed in ice-cold 2.5% perchloric acid (0.9 mL) containing 0.1 mM cAMP, held on ice for 1 h and neutralized with 4.2 M KOH (0.1 mL)). Lineage marker-positive cells were preincubated in a similar manner but the medium contained RMPI instead of serum-free stem cell medium. ATP and cAMP were separated by sequential chromatography on columns containing Dowex AG50-X8 and neutral alumina (12).

The fact that differences can only be seen in the presence of forskolin is a technical problem—the signal is too low in the absence of forskolin-sensitization to see any differences between the different compounds, i.e. ilo-, beraprost and treprostinil. Sensitization means that cells are sensitized for receptor response as these cells contain extremely low cAMP.

According to the concentration-response curve (FIG. 5) for Trepostinil it can be clearly shown that increase of cAMP is significant without addition of forskolin.

Bone Marrow Transplantation:

Isogenic recipient mice were subjected to lethal irradiation. If not rescued by intravenous administration of haematopoetic stem cells, these mice died within the first two weeks. Lin$^-$ (Sca1$^+$ and c-Kit$^+$) haematopoetic stem cells were prepared as outlined above and were pretreated ex vivo in the absence and presence of 10 μM Treprostinil, the combination of Treprostinil+30 μM forskolin (FSK), 10 μg/mL cholera toxin for 1 h at 37° C. Thereafter, the cells (3×10$^5$/mouse) were injected via the tail vein. White blood cell count was determined by FACS. White blood cell counts were determined every 5 days starting on day 9 (where blood cell count was ~1 G/L.

Results

Purification of Haematopoetic Stem Cells:

The MACS-based procedure retains lineage marker-positive (Lin$^+$) cells on the magnetic beads and allows for recovery of lineage marker-negative cells (Lin$^-$): The nature of the cell population was characterized by FACS. The MACS-retained cell population was indeed enriched in cells that stained for lineage-specific markers and were devoid of the stem-cell receptor c-Kit/CD117 (FIG. 1).

In contrast, cells that were recovered from the column flow-through were predominantly found in the upper left quadrant, i.e., they displayed high c-Kit levels and were depleted of APC-Cy7-A fluorescence, which was indicative of depletion of lineage markers (FIG. 2).

The cell populations were further evaluated by staining for both c-Kit and Sca-1 (stem cell antigen-1): the lineage-positive cells were devoid of these two markers (FIG. 3A) whereas the lineage-negative fraction expressed high levels of c-Kit or the combination of c-Kit and Sca-1 (FIG. 3B).

Cyclic AMP Accumulation in c-Kit+ and Sca1$^+$ Cells

The adenine nucleotide pool of the haematopoetic stem cells (c-Kit$^+$ and Sca-1$^+$ population, see FIG. 3B) was metabolically labelled with [$^3$H]adenine and their response to Treprostinil and to other prostaglandin receptor agonists examined. Because these cells have a very modest cAMP response, the enzyme was sensitized by using forskolin. This diterpene binds in the pseudosubstrate cleft between the catalytic C1 and C2 domains of adenylyl cyclase and renders the various isoforms of the enzyme more responsive to the stimulatory G protein G$\alpha_s$ (13-15). As can be seen from FIG. 4, Treprostinil, Beraprost and Iloprost per se caused a modest accumulation of cAMP that was comparable in magnitude to that elicited by 30 μM forskolin. However, when combined with forskolin, Treprostinil caused an increase in cAMP levels that exceeded that caused by the IP-(I prostanoid) receptor-specific compounds Iloprost and Beraprost. This can be rationalized, if the action of treprostinil on EP (E prostanoid)-receptors is taken into account (10). Treprostinil caused a concentration-dependent accumulation of cAMP in the range of 0.1 to 10 μM (FIG. 5). The estimated EC$_{50}$ was in the range of 0.3 μM. Treprostinil failed to increase cAMP levels in the Lin$^+$ haematopoetic cell fraction (data not shown).

Reconstitution of the Bone Marrow by (Lin$^-$, c-Kit$^+$, Sca1$^+$) Haematopoetic Stem Cells Lethally irradiated mice were rescued by the intravenous injection of 3*10$^5$ Lin$^-$, c-Kit$^+$, Sca1$^+$ cells. The white blood cell count started to increase from a nadir on day 9 and slowly increased over the next several weeks. The level of white blood cells at day 60 after injection of haematopoetic stem cells was chosen as the relevant end point, because after 60 days circulating white blood cells could have only been produced from engrafted haematopoetic stem cells. As can be seen from FIG. 6, mice that had been injected with Treprostinil-pretreated haematopoetic stem cells had significantly higher levels of circulating white blood cells than those receiving vehicle-treated haematopoetic stem cells (p<0.05, t-test for unpaired data).

As additional controls, animals were injected with (i) cells treated with cholera toxin, because this is the most effective and persistent activator of Gas, (ii) forskolin, because—as mentioned above—it activates adenylyl cyclase isoforms directly (iii) the combination of forskolin and Treprostinil.

It is evident that Treprostinil was as effective as the positive control cholera toxin which was established as effective ex vivo manipulation (1,2).

Example 2

Isolation of Bone Marrow Stem Cells

C57BL/6 and B6SJL mice were sacrificed and the bone marrow stem cells were isolated as described in Example 1.

In Vitro Pre-Treatment of Isolated Stem Cells

Bone marrow stem cells from C57BL/6 or C6SJL mice were pretreated in vitro with choleratoxin (CTX) or Treprostinil+ Forskolin (FSK) and the stem cells are marked with Ly5.2 or Ly5.1.

In a first experiment, bone marrow stem cells from C57BL/6 mice were used without pretreatment and the stem cells were marked with Ly5.2. Bone marrow stem cells from C6JL were pretreated in vitro with choleratoxin or Treprostinil+ Forskolin and stem cells were marked with Ly5.1.

For comparative studies, a 1:1 mix of Ly5.1+ and Ly5.2+ cells are introduced into mice by bone marrow transplantation and the ratio of Ly5.2 and Ly5.1 positive blood cells was measured initially. Then 16 weeks after bone marrow transplantation blood cells outgrowth was measured. The results are shown in FIG. 7 wherein it is clearly shown that treprostinil/FSK pretreated cells (Ly5.1+) show a significantly increased outgrowth compared to untreated cells and cells pretreated with CT.

In a second experiment, the bone marrow stem cells from C57BL/6 were pretreated in vitro with choleratoxin or Treprostinil+ Forskolin and stem cells were marked with Ly5.2. Bone marrow stem cells from C6JL mice, marked with Ly5.1 were used without any pretreatment.

Again, for comparative studies, a 1:1 mix of Ly5.1+ and Ly5.2+ cells were introduced into mice by bone marrow transplantation and the ratio of Ly5.2 and Ly5.1 positive blood cells was measured initially. Then 16 weeks after bone marrow transplantation blood cells outgrowth was measured. The results are shown in FIG. 8 wherein it is again clearly proven that Treprostinil/FSK pretreated cells (Ly5.2+) show a significantly increased outgrowth compared to untreated cells and cells pretreated with CT. Thus it can be shown that the effect of treprostinil and Forskolin is independent from the origin of the bone marrow cells.

A combination of Treprostinil and forskolin thus increases the engraftment of haematopoetic stem cells and is as or even more effective as pretreatment with cholera toxin.

REFERENCES

1. Adams G B, Alley I R, Chung U I, Chabner K T, Jeanson N T, Lo Celso C, Marsters E S, Chen M, Weinstein L S, Lin C P, Kronenberg H M, Scadden D T (2009) Haematopoietic stem cells depend on Gas-mediated signalling to engraft bone marrow. *Nature* 459:103-107.
2. Dexter T M, Whetton A D, Heyworth C M (1985) Inhibitors of cholera toxin-induced adenosine diphosphate ribosylation of membrane-associated proteins block stem cell differentiation. *Blood* 65:1544-1548.
3. Long M W, Heffner C H, Gragowski L L (1988) Cholera toxin and phorbol diesters synergistically modulate murine hematopoietic progenitor cell proliferation *Exp Hematol.* 16:195-200.
4. Freissmuth M, Gilman A G (1989) Mutations of Gsa designed to alter the reactivity of the protein with bacterial toxins. Substitutions at $ARG^{187}$ result in loss of GTPase activity. *J Biol Chem* 264:21907-21914
5. Aksentijevich I, Flinn I (2002) Chemotherapy and bone marrow reserve: lessons learned from autologous stem cell transplantation. *Cancer Biother Radiopharm* 17:399-403.
6. Awedan A A (2002) High intensity regimens with autologous hematopoietic stem cell transplantation as treatment of multiple myeloma. *Ann Transplant* 7:38-43.
7. North T E, Goessling W, Walkley C R, Lengerke C, Kopani K R, Lord A M, Weber G J, Bowman T V, Jang I H, Grosser T, Fitzgerald G A, Daley G Q, Orkin S H, Zon L I (2007) Prostaglandin E2 regulates vertebrate haematopoietic stem cell homeostasis. *Nature* 447:1007-1011.
8. Hoggatt J, Singh P, Sampath J, Pelus L M (2009) Prostaglandin E2 enhances hematopoietic stem cell homing, survival, and proliferation. *Blood* 113:5444-5455.
9. Goessling W, North T E, Loewer S, Lord A M, Lee S, Stoick-Cooper C L, Weidinger G, Puder M, Daley G Q, Moon R T, Zon L I (2009) Genetic interaction of PGE2 and Wnt signaling regulates developmental specification of stem cells and regeneration. *Cell* 136:1136-1147.
10. Aronoff D M, Peres C M, Serezani C H, Ballinger M N, Carstens J K, Coleman N, Moore B B, Peebles R S, Faccioli L H, Peters-Golden M (2007) Synthetic prostacyclin analogs differentially regulate macrophage function via distinct analog-receptor binding specificities. *J Immunol* 178:1628-1634.
11. Kiriyama M, Ushikubi F, Kobayashi T, Hirata M, Sugimoto Y, and Narumiya S (1997) Ligand binding specificities of the eight types and subtypes of the mouse prostanoid receptors expressed in Chinese hamster ovary cells. *Br J Pharmacol* 122:217-224
12. Johnson R A, Alvarez, R, Salomon, Y. (1994) Determination of adenylyl cyclase catalytic activity using single and double chromatographic procedures. *Methods in Enzymology* 238:31-56
13. Tesmer J J, Sunahara R K, Gilman A G, Sprang S R (1997) Crystal structure of the catalytic domains of adenylyl cyclase in a complex with Gsα. GTPγS. *Science* 278:1907-1916.
14. Sunahara R K, Dessauer C W, Gilman A G (1996) Complexity and diversity of mammalian adenylyl cyclases. *Annu Rev Pharmacol Toxicol* 36:461-480.
15. Kudlacek O, Mitterauer T, Nanoff C, Hohenegger M, Tang W J, Freissmuth M, Kleuss C (2001) Inhibition of adenylyl and guanylyl cyclase isoforms by the antiviral drug foscarnet. *J Biol Chem* 276:3010-3016
16. Otsuka H. et al., The prostacyclin analog beraprost sodium augments the efficacy of therapeutic angiogenesis induced by autologous bone marrow cells, A . . . Vasc. Surg, 2006, 20:646-652
17. Madonna R., "Prostacyclin improves transcoronary myocardial delivery of adipose tissue-derived stromal cells", Europ. Heart Journ., 2006, Vol. 27, No. 17, 2054-2061
18. Ishii M. et al., "Mesenchymal stem cell-based gene therapy with prostacyclin synthase enhanced neovascularisation in hindlimb ischemia", 2009, Vol. 206, No. 1, 109-118
19. Crutchley D. J. et al., "Effects of prostacyclin analogs on the synthesis of tissue factor, tumor necrosis factor-alpha and interleukin-113 in human monocytic THP-1 cells", J. Pharma. and Exp. Therap, 1994, Vol. 271, No. 1, 446-451

The invention claimed is:

1. A method for enhancing engraftment of haematopoietic stem cells (HSCs) by an ex vivo pretreatment of the HSCs which comprises the following steps:
   a. obtaining a sample containing haematopoietic stem cells,
   b. admixing with said sample at least one prostacyclin analogue, wherein the prostacyclin analogue is selected from the group consisting of treprostinil, iloprost, and beraprost or pharmaceutically acceptable salts thereof, and forskolin to obtain a mixture,
- c. incubating said mixture for a period of time sufficient to stimulate G alpha-signalling in said cells, and optionally
- d. isolating said stimulated cells.

2. The method of claim 1, wherein said prostacyclin analogue is treprostinil.

3. The method of claim 1, wherein said sample is bone marrow.

4. The method of claim 1, wherein said stem cells are derived from cord blood, donor bone marrow or placenta.

5. The method of claim 1, further comprising the step of transplanting the HSCs into an individual.

6. The method of claim 1, wherein said prostacyclin analogue is iloprost.

7. The method of claim 1, wherein said prostacyclin analogue is beraprost.

8. The method of claim 5, further comprising the step of administering a composition comprising at least one prostacyclin analogue to the individual.

9. The method of claim 8, wherein the individual suffers from a bone marrow disease selected from the group consisting of leukaemia, a defect of the blood cell compartment, and a bone marrow disease induced by chemotherapy or irradiation.

10. The method of claim 9, wherein said defect of the blood cell compartment is haemoglobinopathy or a defect in neutrophil granulocyte function.

11. The method of claim 8, wherein the prostacyclin analogue administered to the individual is administered for at least 7 days following transplantation of the HSCs into the individual.

12. The method of claim 11, wherein the prostacyclin analogue administered to the individual is administered for at least 10 days following transplantation of the HSCs into the individual.

13. The method of claim 8, wherein the prostacyclin analogue is administered to the individual by a route selected from the group consisting of intravenous administration, subcutaneous administration, and oral administration.

14. The method of claim 13, wherein the prostacyclin analogue is administered orally in a form selected from the group consisting of a sustained release form, a tablet and a capsule.

* * * * *